United States Patent [19]

Habermann et al.

[11] Patent Number: 4,913,780
[45] Date of Patent: Apr. 3, 1990

[54] REDOX ELECTRODE FOR DETERMINING NITROUS ACID AND NITROSYL COMPOUNDS

[75] Inventors: Wolfgang Habermann, Mainz; Peter Hammes, Ruppertsberg; Reinhard Messlinger, Ludwigshafen-Ruchheim; Manered Munzinger, Dirmstein; Helmut Froehlich, Ludwigshafen, all of Fed. Rep. of Germany

[73] Assignee: BASF Aktiengesellschaft, Ludwigshafen, Fed. Rep. of Germany

[21] Appl. No.: 231,383

[22] Filed: Aug. 12, 1988

[30] Foreign Application Priority Data

Aug. 17, 1987 [DE] Fed. Rep. of Germany ....... 3727384

[51] Int. Cl.[4] ................. B01D 59/40; C25B 11/04
[52] U.S. Cl. .................. 204/153.14; 204/290 R; 204/290 F; 204/291; 204/400
[58] Field of Search ............... 204/290 R, 290 F, 291, 204/400

[56] References Cited

U.S. PATENT DOCUMENTS

| | | | |
|---|---|---|---|
| 4,005,003 | 1/1977 | Popplewell et al. | 204/290 F |
| 4,181,754 | 1/1980 | McKinzie et al. | 427/126.3 |
| 4,182,638 | 1/1980 | Cooke | 204/1 T |
| 4,216,071 | 8/1980 | Gobrecht | 204/290 R |
| 4,615,772 | 10/1986 | Hetrick | 204/400 |

Primary Examiner—John F. Niebling
Assistant Examiner—Kathryn Gorgos
Attorney, Agent, or Firm—Keil & Weinkauf

[57] ABSTRACT

A redox electrode for determining nitrous acid and nitrosyl compounds in aqueous, acidic solution consists of a metallic conductor on which an n-conducting metal oxide surface is present.

20 Claims, No Drawings

REDOX ELECTRODE FOR DETERMINING NITROUS ACID AND NITROSYL COMPOUNDS

The present invention relates to a redox electode for determining nitrous acid and nitrosyl compounds in aqueous acidic solution.

For the measurement of nitrous acid and the nitrosyl compounds, the standard platinum redox electrode and redox electrodes of other platinum metals or gold have been tested to date. It has been found that electrodes of these materials are not selective because the potential is determined not only by the nitrous acid but also by oxygen, nitric acid and the diazo compounds formed during the diazotization. Furthermore, the materials described are not sufficiently chemically stable in electrolytes containing nitrosyl compounds and are poisoned by fairly highly concentrated solutions containing nitrous acid. Coating the stated electrode materials with silicone films resulted in a delay in reaching the potential and finally led to the formation of silica and hence to deactivation of the redox electrodes. Doped silicon carbide electrodes became sluggish and inactive due to silica formation, while electrodes containing soluble oxidation products were not selective and did not posses long-term stability.

In the diazotization of primary, aromatic amines or in the reaction of aliphatic amines with nitrous acid, the concentration of the nitrous acid, which also acts as an oxidizing agent in side reactions, must be controlled in order to prevent the formation of undesirable products. Depending on the mineral acid used, nitrous acid is present in the form of nitrosyl halide, nitrosyl sulfate or the nitrosonium ion. Some of the nitrous acid may furthermore be lost for the desired reaction as a result of disproportionation into nitric oxide and nitric acid.

In the purification of nitric acid, the nitrous acid and nitrosyl ions are reduced to concentrations of $<10$ ppm by degassing, making exact determination of the end point necessary. In sewage engineering, agriculture and food chemistry, nitrite as well as other oxidizing agents must be determined quantitatively. To date, these measurements have been very complicated and expensive.

It is an object of the present invention selectively to measure the nitrous acid and the nitrosyl compounds in addition to other oxidizing agents, eg. oxygen or nitric acid, without deactivation of the redox electrode occurring.

We have found that this object is achieved, according to the invention, if a redox electrode is used in which the electrode core consists of a metallic conductor on which an n-conducting metal oxide surface with a conductivity $\kappa$ of from $10^{-7}$ to $1 \times 10^2$ $\Omega^{-1}$ cm$^{-1}$ is present.

The material used for the electrode core is a metallic conductor, eg. platinum, palladium, rhodium, ruthenium, iridium, osmium, copper, silver, gold, titanium, zirconium, hafnium, vanadium, niobium, tantalum, molybdenum, tungsten or an alloy of these metals.

Tungsten, molybdenum, tantalum, niobium and titanium are preferred.

Metal oxides of the metals of subgroups IV to VI of the Periodic Table of elements are applied, as n-conducting oxides, to the electrode cores. Oxides or mixed oxides of tetravalent to hexavalent tungsten and/or molybdenum, trivalent or tetravalent titanium and trivalent to pentavalent vanadium and/or tantalum are preferably used.

The n-conducting metal oxide layers can be applied to the electrode cores, for example, by a vapor deposition method under greatly reduced pressure, chemical gas phase coating or anodic oxidation.

The redox electrodes are prepared using electrode cores in the form of sheets or rods having a smooth and non-porous surface. The purity of the metals is important, so that only metals with a purity of $<99.9\%$ by weight can be used.

Before the claimed oxide surface is produced on the electrode cores, the metal surface is freed from oxides and impurities by ion etching with a noble gas or by mechanical and chemical means. A mixture of hydrofluoric acid, nitric acid and phosphoric acid at temperatures of about $+80°$ C. is suitable for chemical pickling.

The n-conducting metal oxide surface on the electrode cores is preferably produced by anodic oxidation in an aqueous mineral acid. A particularly suitable aqueous mineral acid is 50% strength by weight aqueous sulfuric acid.

The potential of the redox electrode during formation of the oxide film by anodic oxidation should be about 5-10 V. To synthesize a selectively functioning oxide layer of $<100$ Å, an oxidation time of 5-30 minutes is required.

Oxide layers of $<80$ Å do not ensure a sufficient selectivity.

The electrical conductivity $\kappa$ of the metal oxides or mixed oxides should be from $10^{-7}$ to $1 \times 10^2$, preferably from $10^{-6}$ to $1 \times 10^1$, $\Omega^{-1}$.cm$^{-1}$.

The redox electrode is suitable for the amperometric or potentiometric determination of the concentration of nitrous acid and nitrosyl compounds in aqueous, acidic electrolytes; a potentiometric measurement, polarovoltry, is preferably used. In this method of measurement, the redox electrode is cathodically polarized against an auxiliary electrode of platinum or a platinum metal, having a current density of from 0.1 to 5 $\mu$A/cm$^2$ surface area. The measurement of nitrite is carried out by acidification with a non-oxidizing mineral acid, via the nitrous acid liberated.

The open-circuit potential of the redox electrode in the case of cathodic polarization and in the absence of nitrous acid and nitrosyl compounds should be about $+20$ mV relative to the pH-dependent hydrogen evolution potential in the measuring electrolyte.

Calomel, thalamide or silver/silver chloride electrodes are used as reference electrodes for determining the potential, which serves as a parameter for the nitrous acid and the nitrosyl compounds.

If the redox electrode becomes contaminated with coatings, for example with tar-like substances which may occur as byproducts in diazotization, cleaning is possible by means of brief cathodic or anodic polarization for from 1 to 3 minutes using from 10 to 500, preferably from 50 to 200, mA/cm$^2$ surface area. Cleaning is preferably carried out by cathodic polarization. Instead of electrochemical cleaning, chemical cleaning is also possible, for example with about 70% strength by weight sulfuric acid or with organic solvents, such as acetone, dioxane and tetrahydrofuran.

EXAMPLE 1

A tungsten wire consisting of 99.9% of tungsten and having a diameter of 2 mm and a length of 150 mm is surrounded with glass fiber-reinforced teflon, 10 mm of wire at both ends being left exposed for connection of contacts and as a measuring surface. The free measuring surface is freed from impurities and oxide residues by grinding with fine corundum powder and water. After this treatment, the surface is cleaned with acetone and water. To produce the oxide surface, the tungsten electrode is anodically polarized at a potential $\epsilon_h$ of about +5 V against a platinum electrode for about 15 minutes at +25° C. in 50% strength by weight aqueous sulfuric acid. After this treatment, the metallic tungsten core has an oxide surface which possesses a conductivity $\kappa$ of $0.3 \times 10^{-1}$ $\Omega^{-1}$. The measuring electrode, which is ready for use, is cathodically polarized against an auxiliary platinum electrode in 5% strength by weight aqueous hydrochloric acid using a current of 2.3 $\mu$A. A 9 V d.c. voltage source with a 3.88M $\Omega$ series resistor is used for polarization. The potential of the redox electrode is measured at high resistance against a silver/silver chloride reference electrode. After the addition of $NaNO_2$ solution containing hydrochloric acid, the following potentials, based on the $HNO_2$ content, are obtained:

| $HNO_2$ concentration ppm | Potential $\epsilon_h$ mV |
|---|---|
| 1 | +180 |
| 10 | +500 |
| 100 | +770 |
| 1000 | +900 |

If nitric acid is added to the electrolyte containing hydrochloric acid and 1 ppm of $HNO_2$, the potential does not change significantly.

| $HNO_3$ concentration at 1 ppm of $HNO_2$ ppm | Potential $\epsilon_h$ mV |
|---|---|
| 10 | +179 |
| 100 | +182 |

Under the above measuring conditions, a platinum redox electrode indicates the following dependence of the potential on the $HNO_2$ concentration in the $HNO_2$-containing hydrochloric acid.

| $HNO_2$ concentration ppm | Potential $\epsilon_h$ mV |
|---|---|
| 1 | 820 |
| 10 | 860 |
| 100 | 895 |
| 1000 | 840 |

The tungsten electrode is used for the measurement of the $HNO_2$ concentration in the diazotization of aniline in hydrochloric acid-containing solution with sodium nitrite to give benzenediazonium chloride. Aniline and benzenediazonium chloride have no effect on the potential of the redox electrode.

EXAMPLE 2

A tungsten/molybdenum alloy consisting of 95% by weight of tungsten and 5% by weight of molybdenum is pretreated and activated as described in Example 1. the electrical conductivity $\kappa$ of the mixed oxide produced is $5 \times 10^{-3}$ $\Omega^{-1}$ cm$^{-1}$. The measuring electrode, which is ready for use, is cathodically polarized against an auxiliary iridium electrode using a current of 1.73 $\mu$A. A 9 V d.c. voltage source with a 5.2M $\Omega$ series resistor is used for polarization. The redox electrode is used together with a silver/silver chloride reference electrode for measuring nitrous acid and nitrosyl compounds in wastewaters containing sulfuric acid.

EXAMPLE 3

A tungsten electrode is prepared and cleaned as described in Example 1. To produce the oxide surface, the electrode is anodically polarized at a potential $\epsilon_h$ of about +7 V against a platinum electrode for about 25 minutes at +25° C. to 50% strength by weight aqueous sulfuric acid. The electrical conductivity $\kappa$ of the metal oxide produced is $5 \times 10^{-2}$ $\Omega^{-1}$ cm$^{-1}$. The prepared redox electrode is cathodically polarized against an auxiliary platinum electrode using a current of 3.2 $\mu$A. A 9 V d.c. voltage source with a 2.8M $\Omega$ series resistor is used for polarization. The redox electrode is used together with a silver/silver chloride reference electrode for measuring nitrous acid in nitric acid and acidic ammonium nitrate solutions.

In aqueous 10% strength by weight nitric acid, the following potentials, based on the $HNO_2$ content, are obtained:

| $HNO_2$ concentration ppm | Potential $\epsilon_h$ mV |
|---|---|
| 1 | 220 |
| 10 | 480 |
| 100 | 780 |
| 1000 | 880 |

In aqueous 10% strength by weight ammonium nitrate solution having a pH of 1, the following potentials, based on the $HNO_2$ or nitrite content, are measured:

| $HNO_2$ concentration ppm | Potential $\epsilon_h$ mV |
|---|---|
| 1 | 240 |
| 10 | 440 |
| 100 | 630 |
| 1000 | 780 |

We claim:

1. A redox electrode for determining nitrous acid and nitrosyl compounds in aqueous, acidic solution, wherein the electrode core consists essentially of a metallic conductor on which an n-conducting metal oxide surface having a conductivity k of from $10^{-7}$ to $1 \times 10^2$ $\Omega^{-1}$ cm$^{-1}$ is present, and wherein said redox electrode is responsive to the presence of nitrous acid and nitrosyl ions in aqueous acidic solution by producing a potential that correlates to the concentration of the nitrous acid and nitrosyl compounds.

2. The redox electrode of claim 1, wherein a metal of subgroups IV to VI of the Periodic Table of elements is used as the electrode core.

3. The redox electrode of claim 2, wherein a metal selected from the group consisting of tungsten, molybdenum, tantalum, niobium and titanium is used as the electrode core, and wherein the electrical conductivity of the metal oxide surface is from $10^{-6}$ to $1 \times 10^1$ $\Omega^{-1}$ cm$^{-1}$.

4. The redox electrode of claim 1, wherein the n-conducting metal oxide surface consists of an oxide of the elements: tungsten, molybdenum, vanadium, tantalum, titanium or mixtures thereof.

5. The redox electrode of claim 1, wherein the n-conducting metal oxide surface is produced by anodic oxidation of the electrode core in aqueous semiconcentrated sulfuric acid at about room temperature.

6. The redox electrode of claim 1, wherein the anodically produced oxide layer is <100 Å thick.

7. The redox electrode of claim 1, wherein the n-conducting surface consists of a metal oxide of the same metal as the core.

8. A method for determining nitrous acid and nitrosyl concentrations in aqueous acidic solutions, the method comprising:

measuring the potential of a redox electrode against a reference electrode, wherein the redox electrode is cathodically polarized against an auxiliary electrode and the redox electrode has a metallic core and an n-conducting metal oxide surface that has a conductivity of from $10^{-7}$ to $1 \times 10^2$ $\Omega^{-1}$ cm$^{-1}$.

9. The method of claim 8 wherein the redox electrode has a metallic core that consists essentially of one of the metals of subgroups IV to VI of the periodic table.

10. The method of claim 9, wherein the metallic core is made from a metal selected from the group consisting of: tungsten, molybdenum, tantalum, niobium and titanium.

11. The method of claim 8, wherein the n-conducting metal oxide surface consists of an oxide of a metal selected from the group consisting of: tungsten, molybdenum, vanadium, tantalum and titanium.

12. The method of claim 8, wherein the metal oxide surface is greater than 100 Å thick.

13. A redox electrode, comprising:
    (a) a metallic electrode core, and
    (b) an n-conducting metal oxide surface, wherein the n-conducting metal oxide surface resides on the electrode core and has a conductivity k of from $10^{-7}$ to $1 \times 10^2$ $\Omega^{-1}$ cm$^{-1}$, whereby the redox electrode has an ability to determine the concentration of nitrous acid and nitrosyl compounds in an aqueous acidic solution by measuring the electrodes potential against a reference electrode in the solution.

14. The redox electrode of claim 13, wherein the purity of the metal(s) selected for the electrode core is greater than 99.9% by weight.

15. The redox electrode of claim 14, wherein the metallic oxide layer is greater than or equal to 80 Å thick.

16. The redox electrode of claim 15, wherein the metallic oxide layer is greater than 100 Å thick.

17. The redox electrode of claim 14, wherein the electrode core is made from a metal selected from the group consisting of: platinum, palladium, rhodium, ruthenium, iridium, osmium, copper, silver, gold, titanium, zirconium, hafnium, vanadium, niobium, tantalum, molybdenum, tungsten and an alloy of these metals.

18. The redox electrode of claim 17, wherein the electrode core is made from a metal selected from the group consisting of: tungsten, molybdenum, tantalum, niobium and titanium.

19. The redox electrode of claim 13, wherein metal oxides of the subgroups IV to VI of the periodic table are applied as n-conducting oxides.

20. The redox electrode of claim 13, wherein the conductivity of the metal oxide surface is from $10^{-6}$ to $1 \times 10^1$ $\Omega^{-1}$ cm$^{-1}$.

* * * * *

UNITED STATES PATENT AND TRADEMARK OFFICE
CERTIFICATE OF CORRECTION

PATENT NO. : 4,913,780
DATED : April 3, 1990
INVENTOR(S) : Wolfgang HABERMANN et al.

It is certified that error appears in the above-identified patent and that said Letters Patent is hereby corrected as shown below:

Title Page

Co-inventor "Manered Munzinger" should read -- Manfred Munzinger --

Claim 6, line 2

"cally produced oxide layer is $< 100\text{Å}$" should read -- cally produced oxide layer is $> 100\text{Å}$ --

Signed and Sealed this

Twenty-third Day of July, 1991

Attest:

HARRY F. MANBECK, JR.

*Attesting Officer*  *Commissioner of Patents and Trademarks*